(12) United States Patent
Greenspan et al.

(10) Patent No.: US 12,089,895 B2
(45) Date of Patent: Sep. 17, 2024

(54) SYSTEM AND METHOD FOR EVALUATING A VISION OF A SUBJECT

(71) Applicant: SHAMIR OPTICAL INDUSTRY LTD., Kibbutz Shamir (IL)

(72) Inventors: Gvir Greenspan, Kiryat Ata (IL); Gil Lianni, Kibbutz Ma'ayan Baruch (IL); Nili Ruimi, Kfar Blum (IL); Atalia Weiss, Hoshaya (IL); Liron Gleser, Rosh Pina (IL)

(73) Assignee: SHAMIR OPTICAL INDUSTRY LTD., Kibbutz Shamir (IL)

( * ) Notice: Subject to any disclaimer, the term of this patent is extended or adjusted under 35 U.S.C. 154(b) by 0 days.

(21) Appl. No.: 18/001,223

(22) PCT Filed: Sep. 23, 2021

(86) PCT No.: PCT/IL2021/051164
§ 371 (c)(1),
(2) Date: Dec. 8, 2022

(87) PCT Pub. No.: WO2022/064503
PCT Pub. Date: Mar. 31, 2022

(65) Prior Publication Data
US 2023/0190092 A1    Jun. 22, 2023

Related U.S. Application Data

(60) Provisional application No. 63/082,528, filed on Sep. 24, 2020.

(51) Int. Cl.
*A61B 3/02*     (2006.01)
*A61B 3/00*     (2006.01)
(Continued)

(52) U.S. Cl.
CPC ............ *A61B 3/022* (2013.01); *A61B 3/0091* (2013.01); *A61B 3/032* (2013.01); *A61B 3/0325* (2013.01); *A61B 3/113* (2013.01)

(58) Field of Classification Search
CPC ............................... A61B 3/022; A61B 3/0325
(Continued)

(56) References Cited

U.S. PATENT DOCUMENTS 5,436,681 A * 7/1995 Michaels ............... A61B 3/032
                                                              351/239
5,997,142 A * 12/1999 Nakagawa ............. A61B 3/032
                                                              351/221
(Continued)

FOREIGN PATENT DOCUMENTS

| CN | 105307586 | 2/2016 |
|---|---|---|
| CN | 105764405 | 7/2016 |

(Continued)

OTHER PUBLICATIONS

Tanaka, Y., Yokoyama, et al. (2018). Effect of Background Luminance Level on the Assessment of Color Visual Acuity Using Colored Landolt Rings in Young Healthy Subjects. Current Eye Research, 43(3), 428-434. https://doi.org/10.1080/02713683.2017.1405043 (Year: 2018).*

*Primary Examiner* — Zachary W Wilkes
(74) *Attorney, Agent, or Firm* — Pearl Cohen Zedek; LATZER BARATZ LLP

(57) ABSTRACT

A method of evaluating a vision of a subject including: causing a display to define a first display portion and a second display portion; causing the display to emit, from the first display portion, light having a first wavelength value and to emit, from the second display portion, light having a second wavelength value; causing the display to present, on the first display portion, one or more first optotypes and to present, on the second display portion, one or more second (Continued)

optotypes; varying with time the second wavelength value within a predefined wavelengths range; obtaining an indication concerning a subject's perception of the one or more second optotypes as compared to a subject's perception of the one or more first optotypes; and determining a vision disorder of the subject based on the second wavelength value for which the indication has been obtained.

20 Claims, 13 Drawing Sheets

(51) Int. Cl.
*A61B 3/032* (2006.01)
*A61B 3/113* (2006.01)

(58) Field of Classification Search
USPC .................................... 351/237, 242, 201
See application file for complete search history.

(56) References Cited

U.S. PATENT DOCUMENTS

| | | | | |
|---|---|---|---|---|
| 7,568,801 B2* | 8/2009 | Inagaki | ............... | G02B 30/25 351/242 |
| 7,690,790 B2* | 4/2010 | Hosoi | ............... | H04N 13/327 351/242 |
| 7,980,693 B2* | 7/2011 | Reichow | ............... | A61B 3/032 351/246 |
| 8,087,781 B2* | 1/2012 | Kanazawa | ........... | A61B 3/0325 351/239 |
| 9,596,985 B2* | 3/2017 | Ichikawa | ............. | A61B 3/0041 |
| 10,194,795 B2 | 2/2019 | Nauche et al. | | |
| 11,291,362 B2* | 4/2022 | Arnold | ...................... | A61B 3/08 |
| 2005/0219461 A1 | 10/2005 | Hirohara | | |
| 2012/0249951 A1* | 10/2012 | Hirayama | .............. | A61B 3/032 351/201 |
| 2014/0285769 A1* | 9/2014 | Palanker | ................ | G16H 40/67 351/246 |
| 2015/0062530 A1 | 3/2015 | Henry et al. | | |
| 2018/0325369 A1* | 11/2018 | Tang | ........................ | A61B 3/06 |
| 2019/0125180 A1* | 5/2019 | Arnold | ...................... | A61B 3/10 |
| 2021/0076928 A1* | 3/2021 | Grossberg | ............ | A61B 3/0285 |
| 2022/0304572 A1* | 9/2022 | Coveney | .............. | A61B 3/0325 |

FOREIGN PATENT DOCUMENTS

| | | |
|---|---|---|
| CN | 107374581 | 11/2017 |
| CN | 107374581 B | 3/2019 |
| FR | 3014673 | 6/2015 |
| KR | 100855468 A | 2/2008 |

* cited by examiner

| Source | LogWorth | PValue |
|---|---|---|
| Questionnaire | 122.283 | 0.00000 |
| Blue/Cyan-Green | 2.445 | 0.00359 |
| How long do you wear your eyewear for | 2.213 | 0.00612 |
| Snellen | 2.093 | 0.00807 |

*Fig. 8*

| Participant No. | Predicted Correction | Myopic Probability (%) | Hyperopic Probability (%) | No correction needed Probability (%) |
|---|---|---|---|---|
| 1 | Myopic | 86 | 0 | 14 |
| 2 | Hyperopic | 0 | 100 | 0 |
| 3 | No correction needed | 22 | 0 | 78 |

*Fig. 9*

| Participant No. | Test | Myopic Probability (%) |
|---|---|---|
| 1 | Questionnaire | A |
| | Snellen | 6 |
| | Red-Green | Green |
| | Blue/Cyan-Green | 99 |
| | Fan | 30 |
| | Rx error evaluation | Hyperopic correction is required with 99% probability |

| Participant No. | Test | Myopic Probability (%) |
|---|---|---|
| 2 | Questionnaire | A |
| | Snellen | 6 |
| | Red-Green | Green |
| | Blue/Cyan-Green | 106 |
| | Fan | 90 |
| | Rx error evaluation | No correction is required with 78% probability |

*Fig. 10*

| Participant No. | Test | Myopic Probability (%) |
|---|---|---|
| 3 | Questionnaire | D |
|  | Snellen | 4.8 |
|  | Red-Green | Green |
|  | Blue/Cyan-Green | 109 |
|  | Fan | -1 |
|  | Rx error evaluation | Myopic correction is required with 72% probability |

| Participant No. | Test | Myopic Probability (%) |
|---|---|---|
| 4 | Questionnaire | C |
|  | Snellen | 9.5 |
|  | Red-Green | Red |
|  | Blue/Cyan-Green | - |
|  | Fan | 30 |
|  | Rx error evaluation | Myopic correction is required with 98% probability |

*Fig. 10 (cont.)*

SYSTEM AND METHOD FOR EVALUATING A VISION OF A SUBJECT

CROSS-REFERENCE TO RELATED APPLICATIONS

This application is a National Phase Application of PCT International Application No. PCT/IL2021/051164, International Filing Date Sep. 23, 2021, claiming the benefit of U.S. Provisional Patent Application No. 63/082,528, filed Sep. 24, 2020, which are hereby incorporated by reference.

FIELD OF THE INVENTION

The present invention relates to the field of eye care and optometry, and, more particularly, to system and method for evaluating a vision of a subject.

BACKGROUND OF THE INVENTION

Hyperopia is an abnormal condition of an eye in which parallel rays of light are focused behind a retina. This may cause a blurred image and may result from, for example, an eyeball that is too short or from a cornea that is too flat as compared to a normal eye.

Latent hyperopia is an abnormal condition of an eye having mild hyperopia that may be masked when accommodative muscles of the eye are used to increase a focusing power of the eye so as to focus the rays of light onto the retina. Although latent hyperopia is easy to treat, it is difficult to identify due to the subject's ability to compensate with his/her eye accommodation.

SUMMARY OF THE INVENTION

Some embodiments of the present invention may provide a method of evaluating a vision of a subject, which method may include causing a display to define a first display portion and a second display portion, causing the first display portion to emit light having a first wavelength value, causing the second display portion to emit light having a second wavelength value, causing the display to present, on the first display portion emitting light having the first wavelength value, one or more first optotypes, causing the display to present, on the second display portion emitting light having the second wavelength value, one or more second optotypes, varying with time the second wavelength value within a predefined wavelengths range, obtaining an indication that a subject's perception of the one or more second optotypes is substantially the same as a subject's perception of the one or more first optotypes, and determining a vision disorder of the subject based on the second wavelength value for which the indication has been obtained.

Some embodiments may include determining a refractive error of the subject based on the second wavelength value for which the indication has been obtained.

Some embodiments may include determining one or more components of a prescription for a subject's eyewear based on the second wavelength value for which the indication has been obtained.

Some embodiments may include gradually varying the second wavelength value within the predefined wavelengths range at a second wavelength value variation rate.

Some embodiments may include setting the second wavelength value variation rate so that a time interval during which the second wavelength is set to a particular value does not exceed 300 milliseconds.

Some embodiments may include varying the second wavelength value according to an input from the subject or from a third authorized party.

Some embodiments may include alternately and repeatedly presenting the one or more first optotypes and the one or more second optotypes during a first time interval and stopping the presentation thereof for a second time interval.

Some embodiments may include setting the first time interval so that the first time interval does not exceed 300 milliseconds.

Some embodiments may include receiving from the subject the indication that the subject's perception of one or more second optotypes is substantially the same as the subject's perception of the one or more first optotypes.

Some embodiments may include tracking a gaze of the subject with respect to the one or more first optotypes being displayed on the first display portion and generating a first gaze dataset.

Some embodiments may include tracking a gaze of the subject with respect to the one or more second optotypes being displayed on the second display portion and generating a second gaze dataset.

Some embodiments may include determining the indication that the subject's perception of one or more second optotypes is substantially the same as the subject's perception of the one or more first optotypes based on at least a portion of the first gaze dataset and at least a portion of the second gaze dataset.

Some embodiments may include performing an initial screening to gather a personal information concerning the subject.

Some embodiments may include determining the first wavelength value, an initial second wavelength value and the wavelengths range within which the second wavelength value is variable with time based on the personal information.

Some embodiments may include setting the first wavelength value to one of values within a range of 480-600 nanometers.

Some embodiments may include setting the wavelengths range within which the second wavelength value is variable with time to 400-540 nanometers.

Some embodiments may include setting the wavelengths range within which the second wavelength value is variable with time to 560-740 nanometers.

Some embodiments of the present invention may provide a system for evaluating a vision of a subject, which system may include a processing unit configured to: cause a display to define a first display portion and a second display portion, cause the first display portion to emit light having a first wavelength value, cause the second display portion to emit light having a second wavelength value, cause the display to present, on the first display portion emitting light having the first wavelength value, one or more first optotypes, cause the display to present, on the second display portion emitting light having the second wavelength value, one or more second optotypes, vary with time the second wavelength value within a predefined wavelengths range, obtain an indication that a subject's perception of the one or more second optotypes is substantially the same as a subject's perception of the one or more first optotypes, and determine a vision disorder of the subject based on the second wavelength value for which the indication has been obtained.

In some embodiments, the processing unit is configured to determine a refractive error of the subject based on the second wavelength value for which the indication has been obtained.

In some embodiments, the processing unit is configured to determine one or more components of a prescription for a subject's eyewear based on the second wavelength value for which the indication has been obtained.

In some embodiments, the processing unit is configured to gradually vary the second wavelength value within the predefined wavelengths range at a second wavelength value variation rate.

In some embodiments, the processing unit is configured to set the second wavelength value variation rate so that a time interval during which the second wavelength is set to a particular value does not exceed 300 milliseconds.

In some embodiments, the processing unit is configured to vary the second wavelength value according to an input from the subject or from a third authorized party.

In some embodiments, the processing unit is configured to alternately and repeatedly present the one or more first optotypes and the one or more second optotypes during a first time interval and stop the presentation thereof for a second time interval.

In some embodiments, the processing unit is configured to set the first time interval so that the first time interval does not exceed 300 milliseconds.

In some embodiments, the processing unit is configured to receive from the subject the indication that the subject's perception of one or more second optotypes is substantially the same as the subject's perception of the one or more first optotypes.

In some embodiments, the processing unit is interfaceable with a gaze tracking device.

In some embodiments, the gaze tracking device is configured to track a gaze of the subject with respect to the one or more first optotypes being displayed on the first display portion.

In some embodiments, the gaze tracking device is configured to track a gaze of the subject with respect to the one or more second optotypes being displayed on the second display portion.

In some embodiments, the processing unit is further configured to obtain a first gaze dataset determined based on the gaze of the subject being tracked with respect to the one or more first optotypes.

In some embodiments, the processing unit is further configured to obtain a second gaze dataset determined based on the gaze of the subject being tracked with respect to the one or more second optotypes.

In some embodiments, the processing unit is further configured to determine the indication that the subject's perception of one or more second optotypes is substantially the same as the subject's perception of the one or more first optotypes based on at least a portion of the first gaze dataset and at least a portion of the second gaze dataset.

In some embodiments, the processing unit is configured to perform an initial screening to gather a personal information concerning the subject.

In some embodiments, the processing unit is further configured to determine the first wavelength value, an initial second wavelength value and the wavelengths range within which the second wavelength value is variable with time based on the personal information.

In some embodiments, the processing unit is configured to set the first wavelength value to one of values within a range of 480-600 nanometers.

In some embodiments, the processing unit is configured to set the wavelengths range within which the second wavelength value is variable with time to 400-540 nanometers.

In some embodiments, the processing unit is configured to set the wavelengths range within which the second wavelength value is variable with time to 560-740 nanometers.

Some embodiments of the present invention may provide a method of evaluating a vision of a subject, which method may include causing a display to define a first display portion and a second display portion, causing the first display portion to display a background having a first background color, causing the second display portion to present a background having a second background color, causing the display to present, on the first display portion having the first background color, one or more first optotypes, causing the display to present, on the second display portion having the second background color, one or more second optotypes, varying with time the second background color within a predefined background colors range, obtaining an indication that a subject's perception of the one or more second optotypes is substantially the same as a subject's perception of the one or more first optotypes, and determining a vision disorder of the subject based on the second background color for which the indication has been obtained.

Some embodiments may include determining a refractive error of the subject based on the second background color for which the indication has been obtained.

Some embodiments may include determining one or more components of a prescription for a subject's eyewear based on the second background color for which the indication has been obtained.

Some embodiments may include gradually varying the second background color within the predefined background colors range at a second background color variation rate.

Some embodiments may include setting the second background color variation rate so that a time interval during which the second background color is set to a particular color does not exceed 300 milliseconds.

Some embodiments may include varying the second background color according to an input from the subject or from a third authorized party.

Some embodiments may include alternately and repeatedly presenting the one or more first optotypes and the one or more second optotypes during a first time interval and stopping the presentation thereof for a second time interval.

Some embodiments may include setting the first time interval so that the first time interval does not exceed 300 milliseconds.

Some embodiments may include receiving from the subject the indication that the subject's perception of one or more second optotypes is substantially the same as the subject's perception of the one or more first optotypes.

Some embodiments may include tracking a gaze of the subject with respect to the one or more first optotypes being displayed on the first display portion and generating a first gaze dataset.

Some embodiments may include tracking a gaze of the subject with respect to the one or more second optotypes being displayed on the second display portion and generating a second gaze dataset.

Some embodiments may include determining the indication that the subject's perception of one or more second optotypes is substantially the same as the subject's perception of the one or more first optotypes based on at least a portion of the first gaze dataset and at least a portion of the second gaze dataset.

Some embodiments may include performing an initial screening to gather a personal information concerning the subject.

Some embodiments may include determining the first background color, an initial second background color and the background colors range within which the second background color is variable with time based on the personal information.

Some embodiments may include setting an RGB level of the first display portion to [0, 255, 0].

Some embodiments may include setting an RGB level of the second display portion to vary with time within a range of [0, 0, 255] and [0, 255, 255].

Some embodiments of the present invention may provide a system for evaluating a vision of a subject, which system may include a processing unit configured to: cause a display to define a first display portion and a second display portion, cause the first display portion to present a background having a first background color, cause the second display portion to present a background having a second background color, cause the display to present, on the first display portion having the first background color, one or more first optotypes, cause the display to present, on the second display portion having the second background color, one or more second optotypes, vary with time the second background color within a predefined background colors range, obtain an indication that a subject's perception of the one or more second optotypes is substantially the same as a subject's perception of the one or more first optotypes, and determine a vision disorder of the subject based on the second background color for which the indication has been obtained.

In some embodiments, the processing unit is configured to determine a refractive error of the subject based on the second background color for which the indication has been obtained.

In some embodiments, the processing unit is configured to determine one or more components of a prescription for a subject's eyewear based on the second background color for which the indication has been obtained.

In some embodiments, the processing unit is configured to gradually vary the second background color within the predefined background colors range at a second background color variation rate.

In some embodiments, the processing unit is configured to set the second background color variation rate so that a time interval during which the second background color is set to a particular value does not exceed 300 milliseconds.

In some embodiments, the processing unit is configured to vary the second background color according to an input from the subject or from a third authorized party.

In some embodiments, the processing unit is configured to alternately and repeatedly present the one or more first optotypes and the one or more second optotypes during a first time interval and stop the presentation thereof for a second time interval.

In some embodiments, the processing unit is configured to set the first time interval so that the first time interval does not exceed 300 milliseconds.

In some embodiments, the processing unit is configured to receive from the subject the indication that the subject's perception of one or more second optotypes is substantially the same as the subject's perception of the one or more first optotypes.

In some embodiments, the processing unit is interfaceable with a gaze tracking device.

In some embodiments, the gaze tracking device is configured to track a gaze of the subject with respect to the one or more first optotypes being displayed on the first display portion.

In some embodiments, the gaze tracking device is configured to track a gaze of the subject with respect to the one or more second optotypes being displayed on the second display portion.

In some embodiments, the processing unit is further configured to obtain a first gaze dataset determined based on the gaze of the subject being tracked with respect to the one or more first optotypes.

In some embodiments, the processing unit is further configured to obtain a second gaze dataset determined based on the gaze of the subject being tracked with respect to the one or more second optotypes.

In some embodiments, the processing unit is further configured to determine the indication that the subject's perception of one or more second optotypes is substantially the same as the subject's perception of the one or more first optotypes based on at least a portion of the first gaze dataset and at least a portion of the second gaze dataset.

In some embodiments, the processing unit is configured to perform an initial screening to gather a personal information concerning the subject.

In some embodiments, the processing unit is configured to determine the first background color, an initial second background color and the background colors range within which the second background color is variable with time based on the personal information.

In some embodiments, the processing unit is configured to set an RGB level of the first display portion to [0, 255, 0].

In some embodiments, the processing unit is configured to set an RGB level of the second display portion to vary with time within a range of [0, 0, 255] and [0, 255, 255].

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same can be carried into effect, reference will now be made, purely by way of example, to the accompanying drawings in which like numerals designate corresponding elements or sections throughout.

In the accompanying drawings:

FIGS. 7, 8, 9 and 10, showing experimental results obtained during clinical trials to evaluate the multi-step method, according to some embodiments of the invention.

Figure 1:
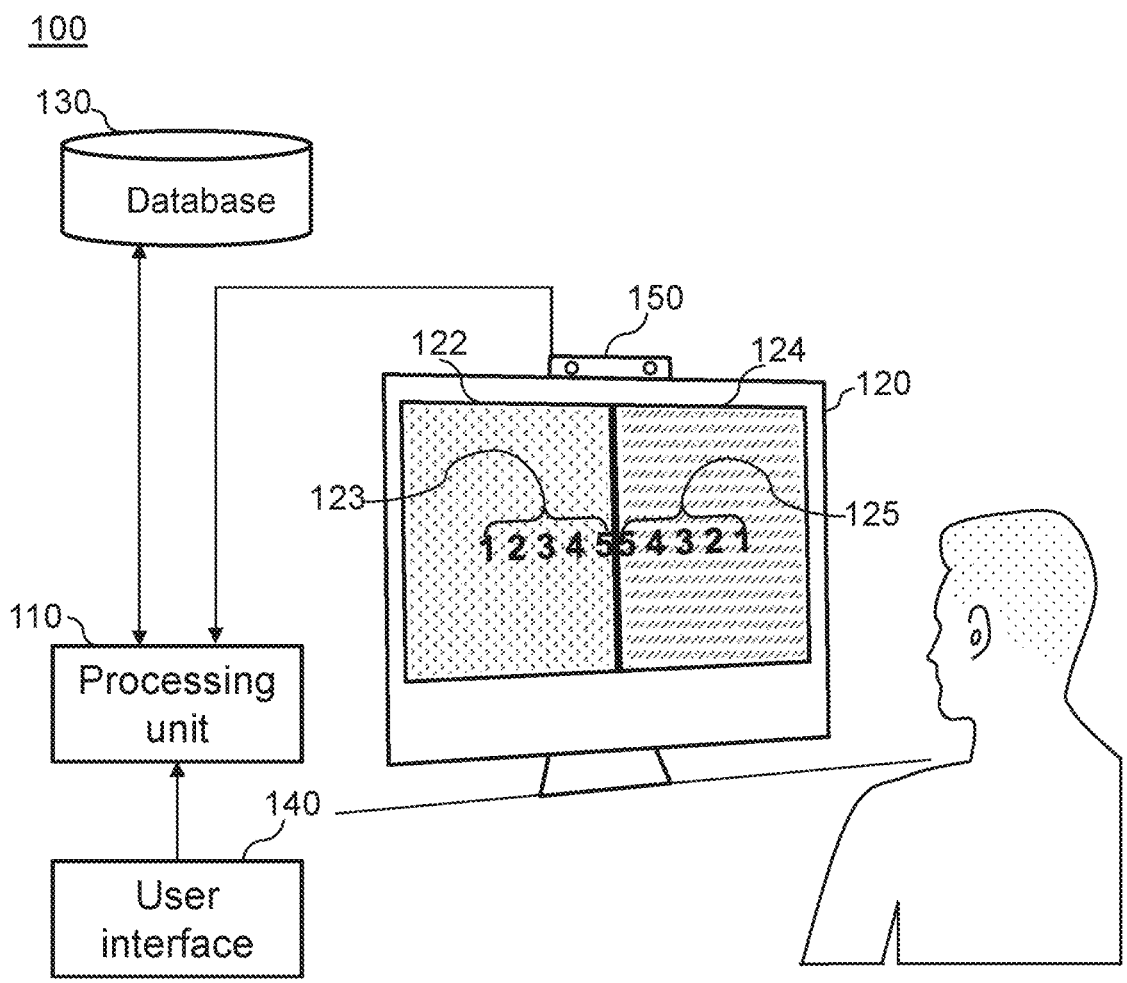
FIG. 1 is a schematic illustration of a system for evaluating a vision of a subject, according to some embodiments of the invention.

It will be appreciated that, for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention can be practiced without the specific details presented herein. Furthermore, well known features can have been omitted or simplified in order not to obscure the present invention. With specific reference to the drawings, it is stressed that the particulars shown are by way of example and for purposes of illustrative discussion of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention can be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that can be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. Any of the disclosed modules or units can be at least partially implemented by a computer processor.

Reference is now made to FIG. 1, which is a schematic illustration of a system 100 for evaluating a vision of a subject, according to some embodiments of the invention.

System 100 may include a processing unit 110. In some embodiments, system 100 may include a display 120. In some embodiments, display 120 may be an external display (e.g., that is not included in the system 100) interfaceable with processing unit 110.

Processing unit 110 may cause display 120 to define two portions on display 120, e.g., a first display portion 122 and a second display portion 124. Processing unit 110 may cause first display portion 122 to emit light having a first wavelength value. Processing unit 110 may cause second display portion 124 to emit light having a second wavelength value. Processing unit 110 may vary with time the second wavelength value within a predefined wavelengths range.

Processing unit 110 may cause display 120 to present one or more first optotypes 123 on first display portion 122 that emits light having the first wavelength value. Processing unit 110 may cause display 120 to present one or more second optotypes 125 on second display portion 124 that emits light having the second wavelength value.

Processing unit 110 may obtain an indication that a subject's perception of second optotype(s) 125 is the same (or substantially the same) as a subject's perception of first optotype(s) 123. Processing unit 110 may determine a vision disorder of the subject based on the second wavelength value for which the indication has been obtained.

The first wavelength value of light being emitted from first display portion 122, the second wavelength value of light being emitted from second display portion 124 and the predefined wavelengths range within which the second wavelength value is variable with time may be set based on the visual disorder for which the subject is being evaluated.

In one example, processing unit 110 may determine a refractive error of a subject caused by hyperopia and/or latent hyperopia. In this example, the first wavelength value may have one of values within a range of 480-600 nanometers. Light having a wavelength value within a range of 480-600 nanometers is being visually perceived by humans as substantially green color. The second wavelength value may be variable with time within the predefined range of 400-540 nanometers. Light having a wavelength value within a range of 400-540 nanometers is being visually perceived by humans as substantially cyan-blue colors. An emmetropic eye (e.g., an eye that has no refractive errors or an eye that is well corrected by, for example, spectacles, contact lenses, etc.) may focus the light being emitted from first display portion 122 and having the first wavelength value of 480-600 nanometers closer to an eye retina than the light being emitted from second display portion 124 and having the second wavelength value of 400-540 nanometers. This may cause first optotype(s) 123 being presented on first display portion 122 to be perceived by the subject having the emmetropic eye as sharper/clearer as compared to second optotype(s) 125 being presented on second display portion 124. A hyperopic eye, or latent hyperopic eye, may focus the light being emitted from second display portion 124 and having the second wavelength value of 400-540 nanometers closer to the eye retina as compared to the emmetropic eye. Thus, while first optotype(s) 123 being presented on first display portion 122 are yet being perceived by the subject having the hyperopic eye as sharp/clear (e.g., like in the case of the emmetropic eye), second optotype(s) 125 being presented on second display portion 124 are being perceived by the subject as clearer/sharper as compared to subject having the emmetropic eye.

During the vision test, processing unit 110 may vary with time the second wavelength value of the light being emitted from second display portion 124 and may obtain an indication that the subject's perception of second optotype(s) 125 is the same (or substantially the same) as the subject's perception of first optotype(s) 123. In some embodiments, processing unit 110 may determine a refractive error of the subject based on the second wavelength value for which the indication has been obtained. For example, a second wavelength value of around 460 nm and 450 nm for which the indication has been obtained, may indicate a refractive error of about +0.5D and +0.75D, respectively.

In some embodiments, processing unit 110 may determine one or more components of a prescription for a subject's eyewear based on the second wavelength value for which the indication has been obtained. The components of the prescription (e.g., commonly referred to as Rx) may be, for example, Sphere (Sph), Cylinder or astigmatism (Cyl), Axis (Ax), Vertical and Horizontal prism, and Addition (Add).

In some embodiments, processing unit 110 may determine the one or more components of the prescription for the subject's eyewear further based on a reference dataset. The reference dataset may, for example, include a predefined data that may relate different second wavelength values to different components of a prescription for an eyewear. In some embodiments, system 100 may include a database 130 that may store the reference dataset. In some embodiments, database 130 may be an external database (e.g., that is not included in system 100) interfaceable with processing unit 110.

In some embodiments, processing unit 110 may determine the one or more components of the prescription for the subject's eyewear further based on a distance between the subject and display 120. In some embodiments, the distance may be known. For example, the subject may be instructed to sit at a specified distance from display 120. In some embodiments, processing unit 110 may determine the distance of the subject from display 120. For example, system 100 may include a camera configured to take one or more images of the subject. The camera may be, for example, positioned on display 120 or may be a built-in camera, etc. Processing unit 110 may determine the distance of the subject from display 120 based on the image(s) from the camera. In some embodiments, the camera may be an external camera (e.g., that is not included in system 100) interfaceable with processing unit 110. In some embodiments, processing unit 110 may determine the distance of the subject from display 120 based on image(s) obtained by a camera of a gaze tracking device 150.

In some embodiments, processing unit 110 may gradually vary the second wavelength value of light being emitted from second display portion 124 within the predefined wavelengths range. In various embodiments, processing unit 110 may gradually increase or decrease the second wavelength value within the predefined wavelengths range. In some embodiments, processing unit 110 may vary the second wavelength value at a second wavelength value variation rate. In various embodiments, the second wavelength value variation rate may be predefined or random. In various embodiments, the second wavelength value variation rate may be constant or may accelerate with time. In some embodiments, the second wavelength value variation rate may be monotonic. In some embodiments, the second wavelength value variation rate is set so that a time interval during which the second wavelength is set to a particular value does not exceed 300 milliseconds. The time interval that does not exceed 300 milliseconds may be short enough so that the subject's eye has not enough time to accommodate itself to the particular wavelength value of light being emitted during that time interval.

In some embodiments, processing unit 110 may vary the second wavelength value of light being emitted from second display portion 124 according to an input from the subject or a third authorized party. For example, the subject/optometrist may use a user interface 140 to select the second wavelength value from the predefined wavelengths range, vary (e.g., increase or decrease) the second wavelength value and/or set the second wavelength value variation rate. In some embodiments, system 100 may include user interface 140. User interface 140 may, for example, include a mouse, a keyboard, etc. For example, a scrolling input from a mouse may be used to vary the second wavelength value manually by the user at a rate according to scroll speed or rotations. In some embodiments, user interface 140 may be an external user interface (e.g., that is not included in system 100) interfaceable with processing unit 110.

In some embodiments, processing unit 110 may present at least one of first optotype(s) 123 and second optotype(s) 125 using a flicker method. For example, during the vision test, processing unit 110 may alternately and repeatedly present first optotype(s) 123 and second optotype(s) 125 during a first time interval and may stop the presentation thereof for a second time interval. In various embodiments, the first time interval and/or the second time interval may be predefined or may be random. For example, the first time interval may not exceed 300 milliseconds such that the subject's eye does not have enough time to accommodate itself to improve perception of the optotype(s) being presented.

In some embodiments, processing unit 110 may receive from the subject the indication that the subject's perception of second optotype(s) 125 is the same (or substantially the same) as the subject's perception of first optotype(s) 123. For example, the subject may be instructed to provide the indication using user interface 140 (e.g., by a mouse or a keyboard click, etc.), or any other input gesture, for example motion, blinking, sound, voice, etc.

In some embodiments, processing unit 110 may automatically determine the indication that the subject's perception of second optotype(s) 125 is the same (or substantially the same) as the subject's perception of first optotype(s) 123. For example, system 100 may include a gaze tracking device 150. Gaze tracking device 150 may track a gaze of the subject with respect to first optotype(s) 123 being displayed on first display portion 122. Gaze tracking device 150 may track a gaze of the subject with respect to second optotype(s) 125 being displayed on second display portion 124. In various embodiments, processing unit 110, gaze tracking device 150 or an external computing device may generate a first gaze dataset and a second gaze dataset based on the gaze being tracked with respect to first optotype(s) 123 and the gaze being tracked with respect to second optotype(s) 125, respectively. Processing unit 110 may determine the indication that the subject's perception of second optotype(s) 125 is the same (or substantially the same) as the subject's perception of first optotype(s) 123 based on at least a portion of the first gaze dataset and at least a portion of the second gaze dataset. For example, processing unit 110 may compare at least a portion of the first gaze dataset with at least a portion of the second gaze dataset and may determine the indication based on the comparison thereof. In some embodiments, gaze tracking device 150 may be an external gaze tracking device (e.g., that is not part of system 100) interfaceable with processing unit 110.

In some embodiments, gaze tracking device 150 may include one or more cameras. In some embodiments, gaze tracking device 150 may include one or more illuminators. In some other embodiments, gaze tracking device 150 may rely on one or more external illuminators. In operation, the illuminator(s) may create one or more patterns of light on the eyes of the subject. The camera(s) of gaze tracking device 150 may take one or more images of the eyes of the user and the pattern(s) of light generated by illuminator(s). In some embodiments, gaze tracking device 150 may include two infrared cameras and one or more infrared illuminators. In some embodiments, gaze tracking device 150 may include one camera and one or more illuminators with structured light. In some embodiments, gaze tracking device 150 may include a single camera (e.g., camera integrated in a mobile device). In some embodiments, gaze tracking device 150 may be wearable by the subject (e.g., gaze tracking device 150 may include a head-mounted camera). In some embodiments, gaze tracking device 150 may operate at a frequency of at least 25-30 Hz. In various embodiments, gaze tracking device 150 may have an accuracy of no more than 1 degree for a gaze angle and/or of no less that 1 mm for a gaze point (e.g., as calculated for the optotypes being displayed on display 120).

First optotype(s) 123 and second optotype(s) 125 may be any optotypes known in the art. For example, first optotype(s) 123 and second optotype(s) 125 may include numbers (e.g., as shown in FIG. 1), letters and/or geometric symbols. For example, first optotype(s) 123 and second optotype(s) 125 may have any color that is different from that of a background color. For example, first optotype(s) 123 and second optotype(s) 125 may have black color. In some embodiments, first optotype(s) 123 and second optotype(s) 125 may be stored in database 130. In some embodiments, database 130 may include information required to render first optotype(s) 123 and second optotype(s) 125. In some embodiments, processing unit 110 may define a size of first optotype(s) 123 and second optotype(s) 125 based on the distance of the subject from display 120. In some embodiments, the subject's perception of first optotype(s) 123 and second optotype(s) 125 may include at least one of a clearance, a sharpness, a contrast, etc. of the optotypes as being observed by the subject on display 120.

In some embodiments, processing unit 110 may perform an initial screening of the subject. For example, the initial screening may be performed prior to the actual vision test. Processing unit 110 may, for example, present on display 120 a set of questions for gathering a personal information concerning the subject and receive answers from the subject, e.g., via user interface 140. The personal information may, for example, include information concerning whether the subject is near sighted or far sighted, information concerning previous vision evaluations (e.g., previous refractive error measurements, previous component(s) of a prescription for a subject's eyewear), an age of the subject, etc. In some embodiments, the personal information for each of the subjects undergoing the testing using system 100 may be saved to database 130.

In some embodiments, processing unit 110 may determine at least one of the first wavelength value, an initial second wavelength value, the wavelengths range within which the second wavelength value may vary with time, the second wavelength value change rate, the first time interval, the second time interval, a type of first optotype(s) 123 and second optotype(s) 125, and a size of first optotype(s) 123 and second optotype(s) 125 based on at least a portion of the personal information of the subject.

Some embodiments of the present invention may provide a non-transitory computer readable medium. The non-transitory computer readable medium may include one or more subsets of instructions that, when executed, cause a processor of a computing device to perform functions such as functions being performed by processing unit 110 as described hereinabove.

Figure 2:
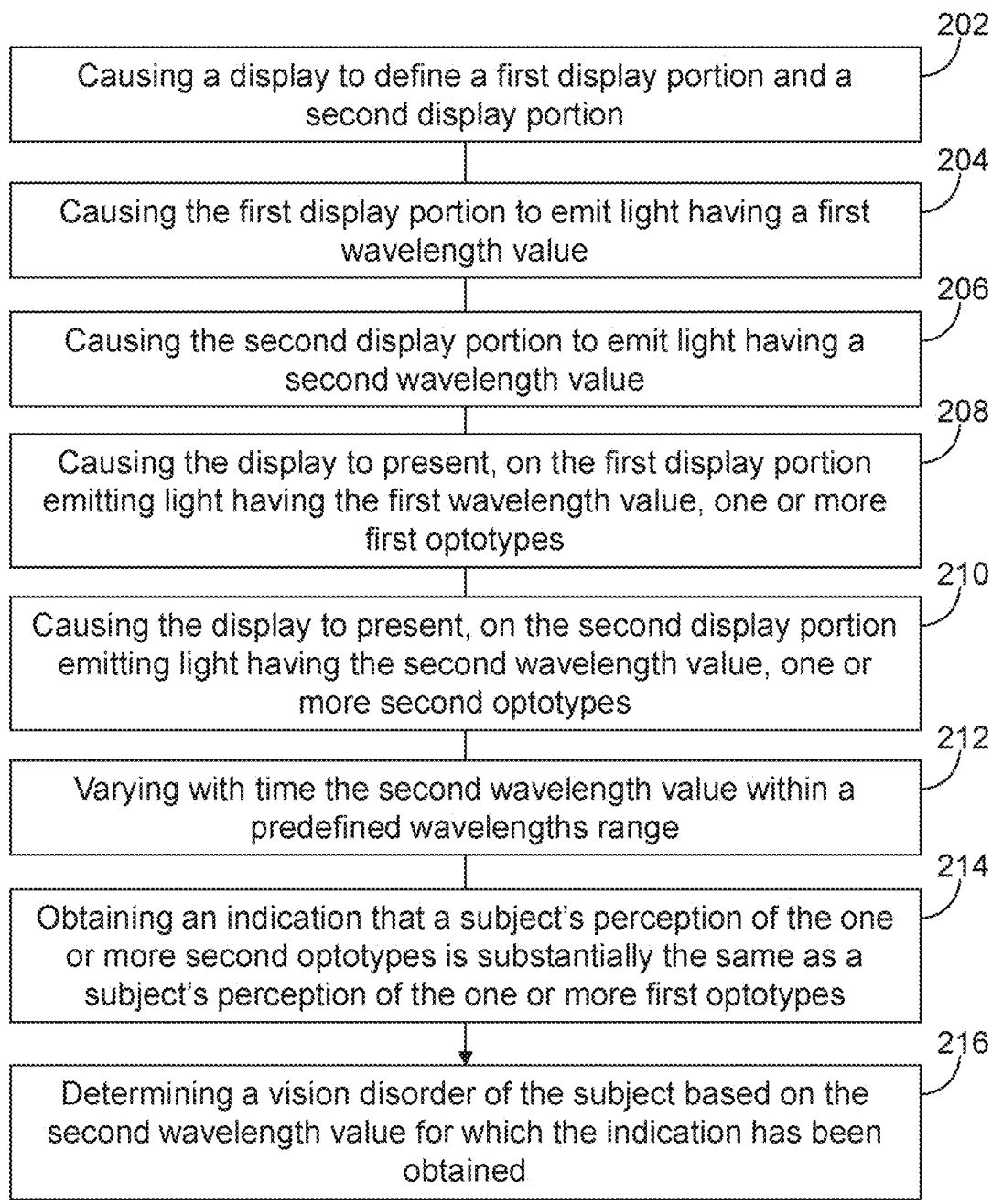
FIG. 2 is a flowchart of a method of evaluating a vision of a subject, according to some embodiments of the invention.

Reference is now made to FIG. 2, which is a flowchart of a method of evaluating a vision of a subject, according to some embodiments of the invention.

The method may include defining 202 a first display portion and a second display portion on a display. For example, as described above with respect to FIG. 1.

The method may include causing 204 the first display portion to emit light having the first wavelength value. For example, as described above with respect to FIG. 1.

The method may include causing 206 the second display portion to emit light having the second wavelength value. For example, as described above with respect to FIG. 1.

The method may include causing 208 the display to present, on the first display portion emitting light having the first wavelength value, one or more first optotypes. For example, as described above with respect to FIG. 1.

The method may include causing 210 the display to present, on the second display portion emitting light having the second wavelength value, one or more second optotypes. For example, as described above with respect to FIG. 1.

The method may include varying 212 with time the second wavelength value within a predefined wavelengths range. For example, as described above with respect to FIG. 1.

The method may include obtaining 214 an indication that a subject's perception of the one or more second optotypes is the same (or substantially the same) as a subject's perception of the one or more first optotypes. For example, as described above with respect to FIG. 1.

The method may include determining 216 a vision disorder of the subject based on the second wavelength value for which the indication has been obtained. For example, as described above with respect to FIG. 1.

Some embodiments may include setting the first wavelength value, the second wavelength value and the predefined wavelengths range within which the second wavelength value is variable with time based on the visual disorder for which the subject is being evaluated. For example, as described above with respect to FIG. 1.

Some embodiments may include setting the first wavelength value to one of values within a range of 480-600 nanometers and setting the wavelength range within which the second wavelength value may vary with time to 400-540 nanometers. These wavelengths may, for example, enable determining a refractive error of the subject caused by hyperopia or latent hyperopia. For example, as described above with respect to FIG. 1.

Some embodiments may include setting the first wavelength value to one of values within a range of 480-600 nanometers and setting the wavelengths range within which the second wavelength value may vary with time to 560-740 nanometers. These wavelengths may, for example, enable determining a refractive error of the subject caused by myopia. For example, as described above with respect to FIG. 1.

Some embodiments may include varying with time the second wavelength value of the light being emitted from the second display portion and obtaining an indication that the subject's perception of the one or more second optotypes is the same (or substantially the same) as the subject's perception of the one or more first optotypes. Some embodiments may include determining a refractive error of the subject based on the second wavelength value for which the indication has been obtained. For example, as described above with respect to FIG. 1.

Some embodiments may include determining one or more components of a prescription for a subject's eyewear based on the second wavelength value for which the indication has been obtained. The components of the prescription (e.g., commonly referred to as Rx) may be, for example, Sphere (Sph), astigmatism (Cyl), Cylinder Axis (Ax), Vertical and Horizontal prism, and Addition (Add). For example, as described above with respect to FIG. 1.

Some embodiments may include determining the one or more components of the prescription for the subject's eyewear further based on a reference dataset. The reference dataset may, for example, include a predefined data that may relate different second wavelength values to different components of a prescription for an eyewear. For example, as described above with respect to FIG. 1.

Some embodiments may include determining the one or more components of the prescription for the subject's eyewear further based on a distance between the subject and the display. In some embodiments, the distance may be known. For example, the subject may be instructed to sit at a known distance from the display. Some embodiments may include determining the distance of the subject from the display. Some embodiments may include obtaining one or more images of the subject using a camera disposed on the display. Some embodiments may include determining the distance of the subject from the display based on the one or more images thereof.

Some embodiments may include gradually varying the second wavelength value of light being emitted from the second display portion within the predefined wavelengths range. Various embodiments may include gradually increasing or decreasing the second wavelength value within the predefined wavelengths range. Some embodiments may include varying the second wavelength value at a second wavelength value variation rate. Various embodiments may include predefining or randomly selecting the second wavelength value change rate. Some embodiments may include setting the second wavelength value variation rate so that a time interval during which the second wavelength is set to a particular value does not exceed 300 milliseconds. The time interval that does not exceed 300 milliseconds may be short enough such that the subject's eye does not have enough time to accommodate itself to the particular wavelength value of light being emitted during that time interval. For example, as described above with respect to FIG. 1.

Some embodiments may include varying the second wavelength value of light being emitted from the second display portion according to an input from the subject or a third authorized party. For example, as described above with respect to FIG. 1.

Some embodiments may include presenting at least one of the one or more first optotypes and the one or more second optotypes using a flicker method. Some embodiments may include alternately and repeatedly presenting the one or more first optotypes and the one or more second optotypes during a first time interval and stopping the presentation thereof for a second time interval. Various embodiments may include predefining or randomly setting the first time interval and/or the second time interval. Some embodiments may include setting the first time interval so that the first time interval does not exceed 300 milliseconds. For example, as described above with respect to FIG. 1.

Some embodiments may include receiving from the subject the indication that the subject's perception of one or more second optotypes is the same (or substantially the same) as the subject's perception of the one or more first optotypes. For example, as described above with respect to FIG. 1.

Some embodiments may include automatically determining the indication that the subject's perception of the one or more second optotypes is the same (or substantially the same) as the subject's perception of the one or more first optotypes. Some embodiments may include tracking a gaze of the subject with respect to the one or more first optotypes being displayed on the first display portion. Some embodiments may include tracking a gaze of the subject with respect to the one or more second optotypes being displayed on the second display portion. Some embodiments may include generating a first gaze dataset and a second gaze dataset based on the gaze being tracked with respect to the one or more first optotypes and the gaze being tracked with respect to the one or more second optotypes, respectively. Some embodiments may include determining the indication that the subject's perception of one or more second optotypes is the same (or substantially the same) as the subject's perception of the one or more first optotypes based on at least a portion of the first gaze dataset and at least a portion of the second gaze dataset. For example, some embodiments may include comparing at least a portion of the first gaze dataset with at least a portion of the second gaze dataset and determining the indication based on the comparison thereof. For example, as described above with respect to FIG. 1.

Some embodiments may include performing an initial screening of the subject. For example, the initial screening may be performed prior to the actual vision test. Some embodiments may include presenting on the display a set of questions for gathering a personal information concerning the subject and receiving answers from the subject. The personal information may, for example, include information concerning whether the subject is near sighted or far sighted, information concerning previous vision evaluations (e.g., previous refractive error measurements, previous component(s) of a prescription for a subject's eyewear), an age of the subject, etc. Some embodiments may include saving to a database the personal information for each of the subjects undergoing the testing. For example, as described above with respect to FIG. 1.

Some embodiments may include determining at least one of the first wavelength value, an initial second wavelength value, the wavelengths range within which the second wavelength value may vary with time, the second wavelength value change rate, the first time interval, the second time interval, a type of the one or more first optotypes and the one or more second optotypes, and a size of the one or more first optotypes and the one or more second optotypes based on at least a portion of the personal information of the subject. For example, as described above with respect to FIG. 1.

Figure 3:
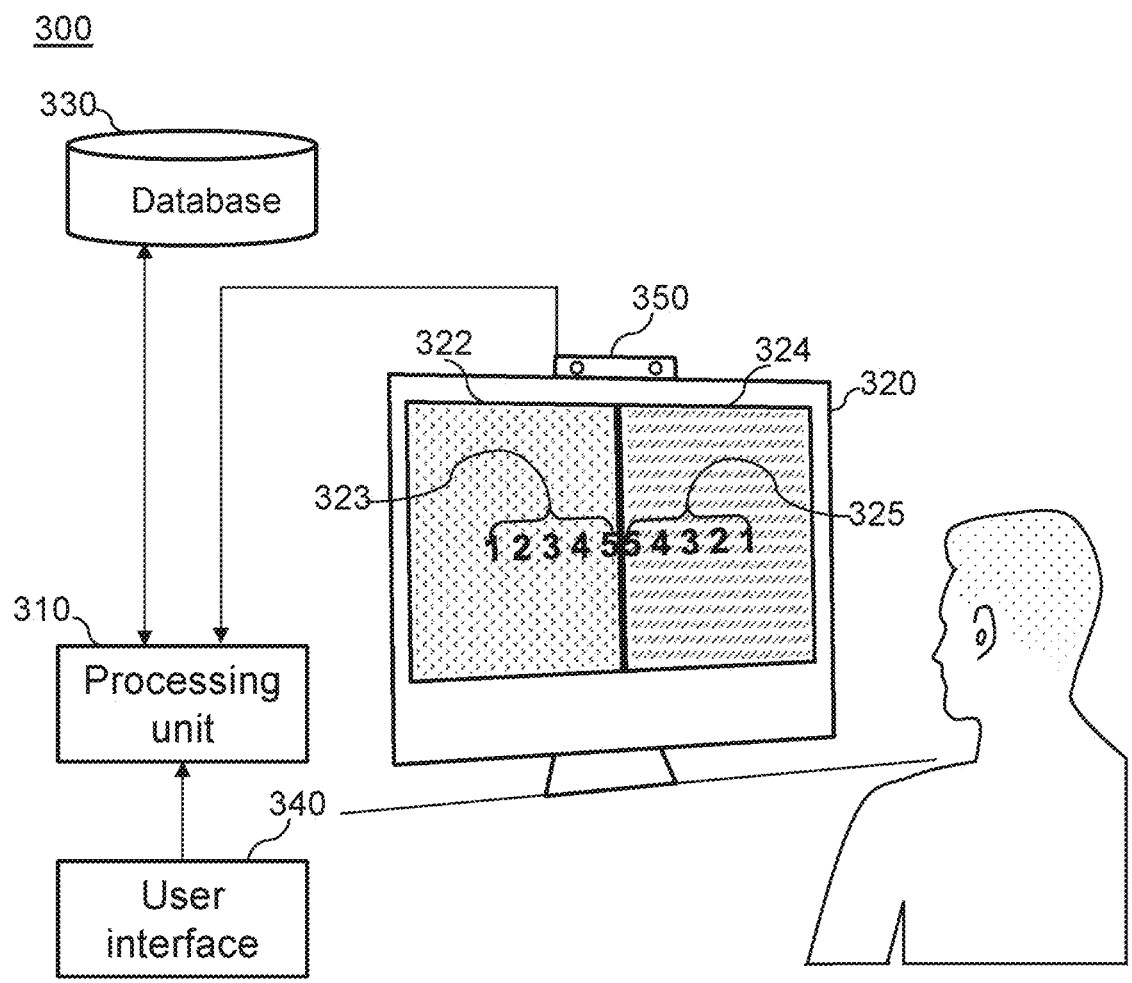
FIG. 3 is a schematic illustration of one embodiment of a system for evaluating a vision of a subject, according to some embodiments of the invention.

Reference is now made to FIG. 3, which is a schematic illustration of one embodiment of a system 300 for evaluating a vision of a subject, according to some embodiments of the invention.

System 300 may include a processing unit 310. In some embodiments, system 300 may include a display 320. In some embodiments, display 320 may be an external display (e.g., that is not included in the system 300) interfaceable with processing unit 310.

Processing unit 310 may cause display 320 to define two portions on display 320, e.g., a first display portion 322 and a second display portion 324. Processing unit 310 may cause first display portion 322 to present a background having a first background color. Processing unit 310 may cause second display portion 324 to present a background having a second background color. Processing unit 310 may vary with time the second background color within a predefined background colors range.

Processing unit 310 may cause display 320 to present one or more first optotypes 323 on first display portion 322 having the first background color. Processing unit 310 may cause display 320 to present one or more second optotypes 325 on second display portion 324 having the second background color. First optotype(s) 323 and second optotype(s) 325 may be similar to first optotype(s) 123 and second optotype(s) 125 described above with respect to FIG. 1.

Processing unit 310 may obtain an indication that a subject's perception of second optotype(s) 325 is the same (or substantially the same) as a subject's perception of first optotype(s) 323. For example, processing unit 310 may receive the indication from the subject (e.g., using a user interface 340, as described above with respect to FIG. 1). In another example, processing unit 310 may automatically determine the indication (e.g., based on gaze datasets from a gaze tracking device 350, as described above with respect to FIG. 1).

Processing unit 310 may determine a vision disorder of the subject based on the second background color of the predefined background colors range for which the indication has been obtained. The first background color, the second background color and the predefined background colors range within which the second background color is variable with time may be set based on the visual disorder for which the subject is being evaluated.

In one example, processing unit 310 may determine a refractive error of a subject caused by hyperopia and/or latent hyperopia. In this example, the first background color may be a substantially green color. For example, processing unit 310 may set an RGB (red, green, blue) level of first display portion 322 to [0, 255, 0]. The second background color may be variable with time within the predefined background colors range of substantially cyan-blue colors. For example, processing unit 310 may set an RGB level of second display portion 322 to vary with time within a range of [0, 0, 255] and [0, 255, 255]. An emmetropic eye (e.g., an eye that has no refractive errors or an eye that is well corrected by, for example, spectacles, contact lenses, etc.) may focus the light being emitted from first display portion 322 having the first background color (e.g., substantially green color) closer to an eye retina than the light being emitted from second display portion 324 having the second background color (e.g., substantially cyan-blue colors). This may cause first optotype(s) 323 being presented on first display portion 322 to be perceived by the subject having the emmetropic eye as sharper/clearer as compared to second optotype(s) 325 being presented on second display portion 324. A hyperopic eye, or latent hyperopic eye, may focus the light being emitted from second display portion 324 having the second background color (e.g., substantially cyan-blue colors) closer to the eye retina as compared to the emmetropic eye. Thus, while first optotype(s) 323 being presented on first display portion 322 are yet being perceived by the subject having the hyperopic eye as sharp/clear (e.g., like in the case of the emmetropic eye), second optotype(s) 325 being presented on second display portion 324 are being perceived by the subject as clearer/sharper as compared to subject having the emmetropic eye.

During the vision test, processing unit 310 may vary with time the second background color within the predefined background colors range and may obtain an indication that the subject's perception of second optotype(s) 325 is the same (or substantially the same) as the subject's perception of first optotype(s) 323. In some embodiments, processing unit 310 may determine a refractive error of the subject based on the second background color for which the indication has been obtained. For example, an RGB value of the second background color of around [0,117,255] and [0,70,255] for which the indication has been obtained, may indicate a refractive error of about +0.5D and +0.75D, respectively. In some embodiments, processing unit 310 may determine one or more components of a prescription for a subject's eyewear based on the second background color for which the indication has been obtained. The components of the prescription (e.g., commonly referred to as Rx) may be, for example, Sphere (Sph), Cylinder or astigmatism (Cyl), Axis (Ax), Vertical and Horizontal prism, and Addition (Add).

In some embodiments, processing unit 310 may determine the one or more components of the prescription for the subject's eyewear further based on a reference dataset. The reference dataset may, for example, include a predefined data that may relate different second background colors (e.g., different RGB levels) to different components of a prescription for an eyewear. In some embodiments, system 300 may include a database 330 that may store the reference dataset. In some embodiments, database 330 may be an external database (e.g., that is not included in system 300) interfaceable with processing unit 310.

In some embodiments, processing unit 310 may determine the one or more components of the prescription for the subject's eyewear further based on a distance between the subject and display 320. In some embodiments, the distance may be known. In some embodiments, processing unit 310 may determine the distance of the subject from display 320 (e.g., as described above with respect to FIG. 1).

In some embodiments, processing unit 310 may gradually vary the second background color of second display portion 324 within the predefined background colors range. In various embodiments, processing unit 310 may gradually increase or decrease the RGB level of second display portion 324. In some embodiments, processing unit 310 may vary the second background color at a second background color variation rate. In various embodiments, the second background color variation rate may be predefined or random. In various embodiments, the second background color variation rate may be constant or may accelerate with time. In some embodiments, the second background color variation rate may be monotonic. In some embodiments, the second background color variation rate is set so that a time interval during which the second background color is set to a particular color within the predefined background colors range does not exceed 300 milliseconds. The time interval that does not exceed 300 milliseconds may be short enough so that the subject's eye has not enough time to accommodate itself to the particular background color being presented during that time interval.

In some embodiments, processing unit 310 may vary the second background color of second display portion 324 according to an input from the subject or a third authorized party. For example, the subject/optometrist may use a user interface 340 to select the RGB level of second display portion 324, vary (e.g., increase or decrease) the RGB level of second display portion 324 and/or set the second background color variation rate.

In some embodiments, processing unit 310 may present at least one of first optotype(s) 323 and second optotype(s) 325 using a flicker method (e.g., as described above with respect to FIG. 1).

In some embodiments, processing unit 310 may perform an initial screening of the subject (e.g., as described above with respect to FIG. 1). In some embodiments, processing unit 310 may determine at least one of the first background color, an initial second background color, the background colors range within which the second background color may vary with time, the second background color change rate, a type of first optotype(s) 323 and second optotype(s) 325, and a size of first optotype(s) 323 and second optotype(s) 325 based on at least a portion of the personal information of the subject (e.g., as described above with respect to FIG. 1).

Some embodiments of the present invention may provide a non-transitory computer readable medium. The non-transitory computer readable medium may include one or more subsets of instructions that, when executed, cause a processor of a computing device to perform functions such as functions being performed by processing unit 310 as described hereinabove.

Figure 4:
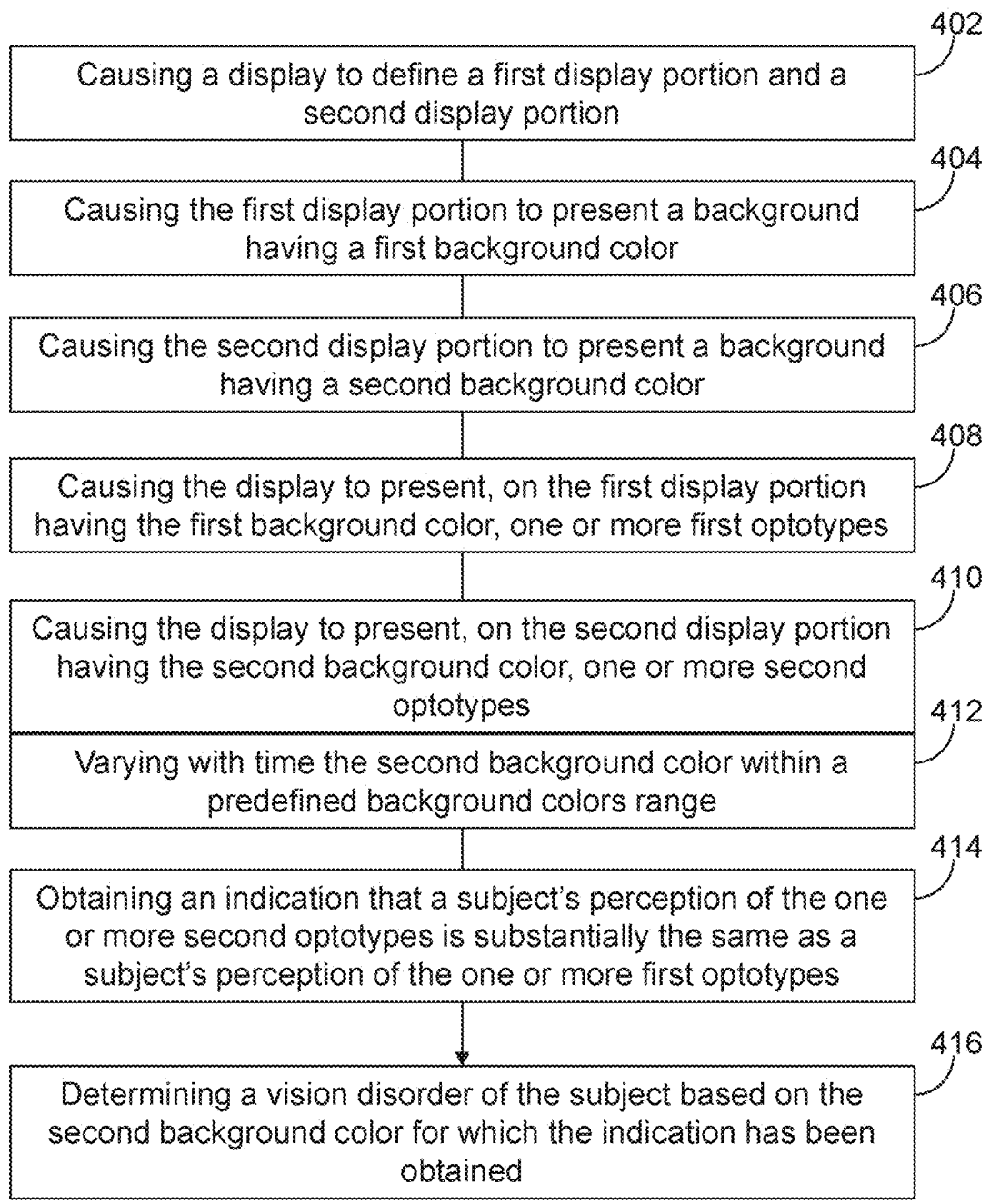
FIG. 4 is a flowchart of one embodiment of a method of evaluating a vision of a subject, according to some embodiments of the invention.

Reference is now made to FIG. 4, which is a flowchart of one embodiment of a method of evaluating a vision of a subject, according to some embodiments of the invention.

The method may include defining 402 a first display portion and a second display portion on a display. For example, as described above with respect to FIG. 3.

The method may include causing 404 the first display portion to present a background having a first background color. For example, as described above with respect to FIG. 3.

The method may include causing 406 the second display portion to present a background having a second background color. For example, as described above with respect to FIG. 3.

The method may include causing 408 the display to present, on the first display portion having the first background color, one or more first optotypes. For example, as described above with respect to FIG. 3.

The method may include causing 410 the display to present, on the second display portion having the second background color, one or more second optotypes. For example, as described above with respect to FIG. 3.

The method may include varying 412 with time the second background color within a predefined background colors range. For example, as described above with respect to FIG. 3.

The method may include obtaining 414 an indication that a subject's perception of the one or more second optotypes is the same (or substantially the same) as a subject's perception of the one or more first optotypes. For example, as described above with respect to FIG. 3.

The method may include determining 416 a vision disorder of the subject based on the second background color for which the indication has been obtained. For example, as described above with respect to FIG. 3.

Some embodiments may include setting the first background, the second background color and the predefined background colors range within which the second background color is variable with time based on the visual disorder for which the subject is being evaluated. For example, as described above with respect to FIG. 3.

Some embodiments may include setting the first background color to a substantially green color and setting the background colors range within which the second background color may vary with time to substantially cyan-blue colors. For example, some embodiments may include setting the RGB level of the first display portion to [0, 255, 0] and setting the RGB level of the second display portion to vary with time within a range of [0, 0, 255] and [0, 255, 255]. These background colors/RGB levels may, for example, enable determining a refractive error of the subject caused by hyperopia or latent hyperopia. For example, as described above with respect to FIG. 3.

Some embodiments may include varying with time the second background color of the second display portion and obtaining an indication that the subject's perception of the one or more second optotypes is the same (or substantially the same) as the subject's perception of the one or more first optotypes. Some embodiments may include determining a refractive error of the subject based on the second background color for which the indication has been obtained. For example, as described above with respect to FIG. 3.

Some embodiments may include determining one or more components of a prescription for a subject's eyewear based on the second background color of the predefined background colors range for which the indication has been obtained. For example, as described above with respect to FIG. 3.

Some embodiments may include determining the one or more components of the prescription for the subject's eyewear further based on a reference dataset. The reference dataset may, for example, include a predefined data that may relate different second background colors to different components of a prescription for an eyewear. For example, as described above with respect to FIG. 3.

Some embodiments may include determining the one or more components of the prescription for the subject's eyewear further based on a distance between the subject and the display. For example, as described above with respect to FIG. 3.

Some embodiments may include gradually varying the second background color of the second display portion within the predefined background colors range. Various embodiments may include gradually increasing or decreasing the RGB level of the second display portion within a predefined RGB levels range. Some embodiments may include varying the second background color at a second background color variation rate. Various embodiments may include predefining or randomly selecting the second background color change rate. Some embodiments may include setting the second background color variation rate so that a time interval during which the second background color is set to a particular color does not exceed 300 milliseconds. The time interval that does not exceed 300 milliseconds may be short enough such that the subject's eye does not have enough time to accommodate itself to the particular background color being present for that time interval. For example, as described above with respect to FIG. 3.

Some embodiments may include varying the second background color of the second display portion according to an input from the subject or a third authorized party. For example, as described above with respect to FIG. 3.

Some embodiments may include presenting at least one of the one or more first optotypes and the one or more second optotypes using a flicker method. For example, as described above with respect to FIG. 3.

Some embodiments may include performing an initial screening of the subject. Some embodiments may include determining at least one of the first background color, an initial second background color, the background colors range within which the second background color may vary with time, the second background color value change rate, a type of the one or more first optotypes and the one or more second optotypes, and a size of the one or more first optotypes and the one or more second optotypes based on at least a portion of the personal information of the subject. For example, as described above with respect to FIG. 3.

Advantageously, the disclosed system and method may provide a tool for evaluating a vision of a subject, for example for determining and quantifying refractive errors caused by hyperopia, latent hyperopia, by myopia, and by astigmatism. The tool may be utilized remotely. For example, a subject may undergo the vision test at subject's home under remote supervision of an optometrist. In some embodiments, the tool may be used to identify subjects having latent hyperopia without a need in drugs that temporarily disable accommodation of the subject's eye (e.g., atropine). For example, the tool may be configured to operate such that the subject's eye does not have enough time to accommodate itself to the stimuli being presented (e.g., as described above with respect to FIGS. 1, 2, 3 and 4).

According to some embodiments of the present invention, systems and methods for evaluating a vision of a subject disclosed hereinabove with respect to FIGS. 1, 2, 3 and 4 may be implemented in a multi-step method of determining one or more components of a prescription for a subject's eyewear.

Figure 5:
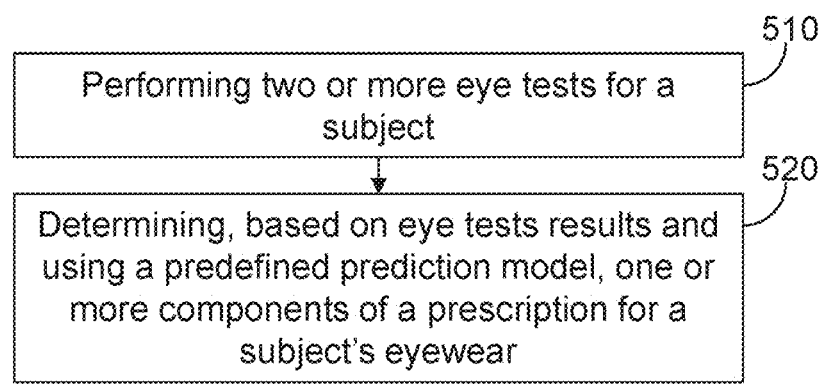
FIG. 5 is a flowchart of a multi-step method of determining one or more components of a prescription for a subject's eyewear, according to some embodiments of the invention.

Reference is now made to FIG. 5, which is a flowchart of a multi-step method of determining one or more components of a prescription for a subject's eyewear, according to some embodiments of the invention.

According to some embodiments of the invention, the multi-step method may include performing 510 two or more eye tests for a subject, and determining 520, based on eye tests results and using a predefined prediction model, one or more components of a prescription for a subject's eyewear.

In some embodiments, the prediction model may be defined based on a data being collected from multiple subjects (e.g., big data). For example, a statistical weight and/or strength of the two or more eye tests may be calculated based on the collected data to define the prediction model. In some embodiments, additional data may be used to define the prediction model. For example, a statistical weight of a subject's age and/or time of last refraction may be calculated and implemented in the prediction model.

In some embodiments, the one or more components of the prescription for the subject's eyewear may be determined based on the eye tests results using the predefined prediction model and further based on a distance of a subject from a display on which the eye tests are being presented.

Prediction model may utilize other methods for determining one or more components of a prescription for a subject's eyewear based on eye tests results and, optionally, based on the distance of the subject from the display on which the eye tests are being presented. Other methods may, for example, include one or more machine learning methods.

Reference is now made to FIGS. 6A, 6B, 6C, 6D and 6E, which are schematic illustrations of eye tests of multi-step method of determining one or more components of a prescription for a subject's eyewear, according to some embodiments of the invention.

Figure 6A:
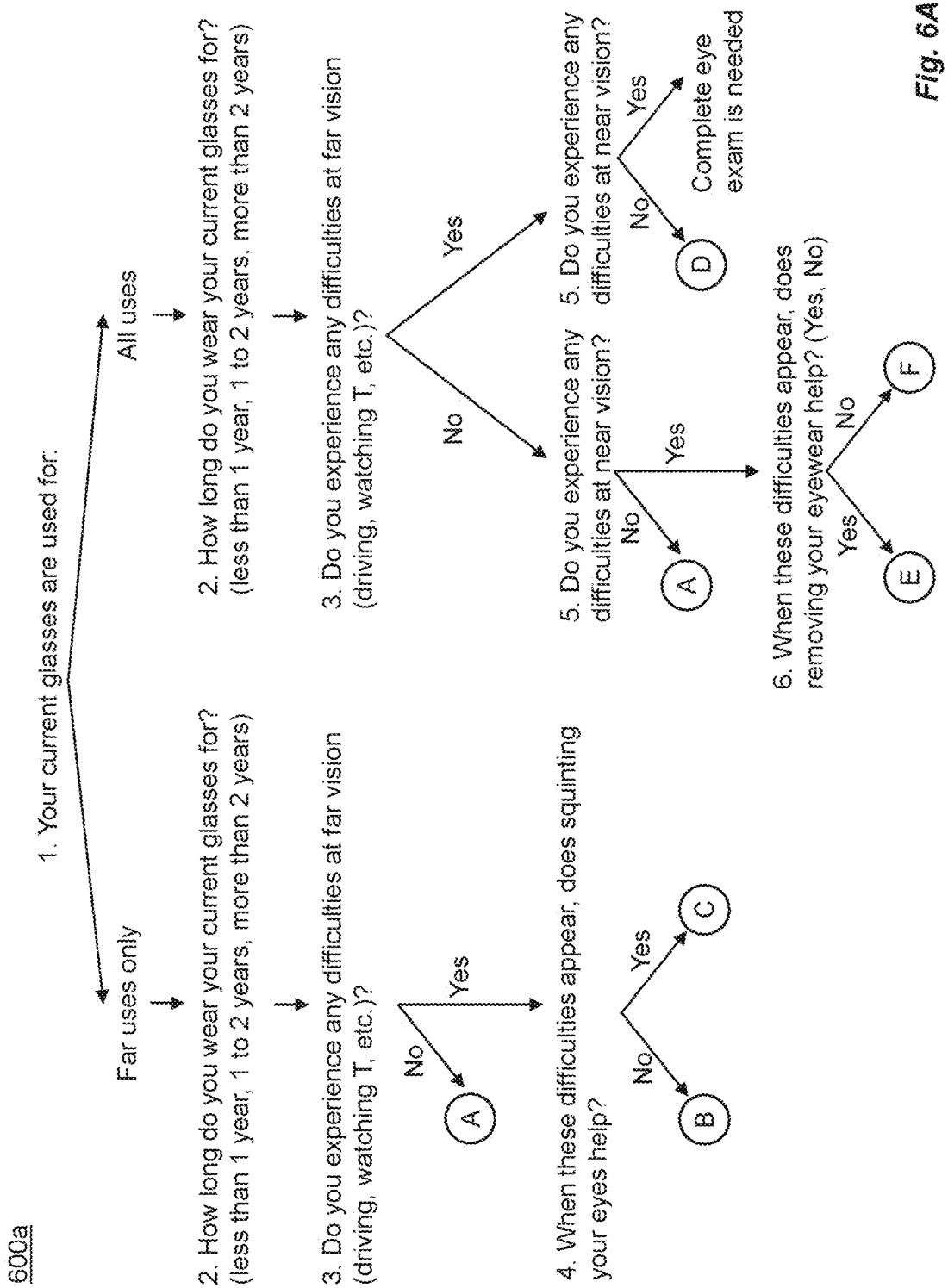
FIGS. 6A, 6B, 6C, 6D and 6E, which are schematic illustrations of eye tests of multi-step method of determining one or more components of a prescription for a subject's eyewear, according to some embodiments of the invention.
Figure 6B:
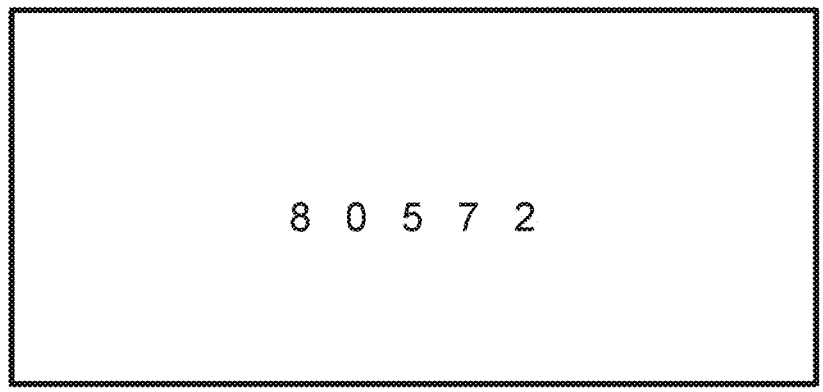

In some embodiments, the multi-step method may include a questionnaire. The subject undergoing the multi-step method may be asked to answer the questionnaire. One example of a questionnaire 600a is shown in FIG. 6A. Questionnaire 600a may, for example, include questions such as (i) whether the subject's eyewear being used for far uses only or for all uses?; (ii) how long does the subject wear their eyewear (e.g., less than 1 year, 1-2 years, more than 2 years)?; (iii) does the subject experience any difficulties at far vision (e.g., driving, TV watching, etc.)?; (iv) when difficulties appear, does squinting the eyes help?; (v) does the subject experience any difficulties at near vision?; (vi) when difficulties appear, does removing the eyewear help? The method may include determining a questionnaire result based on subject's answers. For example, questionnaire 600a result may include six possible outputs being determined based on subject's answers to questionnaire 600a (e.g., outcomes A-F). In this example, questionnaire 600a result may include a recommendation to perform a complete eye examination procedure for the subject. Questionnaire 600a may include additional and/or different questions as well.

In some embodiments, the multi-step method may include a Snellen eye test. One example of a Snellen eye test 600b is show in FIG. 6B. For example, a Snellen eye test 600b result may include a numeric continuous output indicative of a visual acuity of the subject.

Figure 6C:
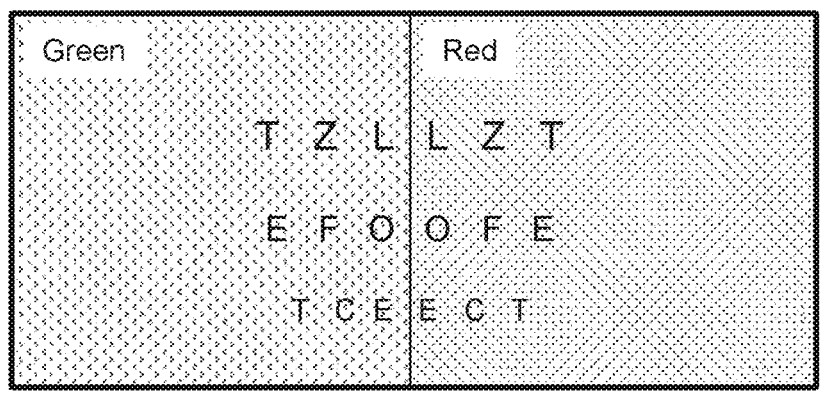

In some embodiments, the multi-step method may include a Red-Green eye test. One example of a Red-Green eye test 600c is shown in FIG. 6C. For example, a Red-Green eye test 600c result may include three possible outputs—e.g., "Green", "Red" or "Equal"—indicative of hyperopic, myopic or no correction required for the subject's eye. For example, if a subject's perception of the optotypes being displayed on the first display portion having green background color is better than a subject's perception of the optotypes being displayed on the second display portion having red background color, the Red-Green eye test 600c result may include "Green" output. In this example, if a subject's perception of the optotypes being displayed on the second display portion having red background color is better than a subject's perception of the optotypes being displayed on the first display portion having green background color, the Red-Green eye test 600c result may include "Red" output. In this example, if a subject's perception of the optotypes being displayed on the second display portion having red background color is the same (or substantially the same) than a subject's perception of the optotypes being displayed on the first display portion having green background color, the Red-Green eye test 600c result may include "Equal" output.

Figure 6D:
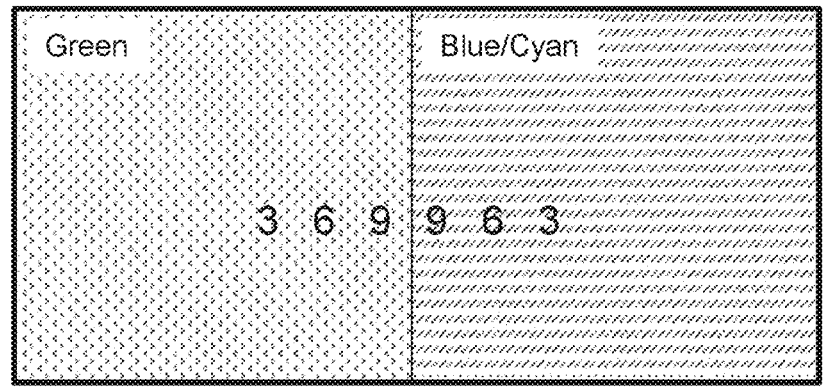

In some embodiments, the multi-step method may include a Blue/Cyan-Green eye test. One example of a Blue/Cyan-Green eye test 600d is shown in FIG. 6D. The Blue/Cyan-Green eye test 600d may be a method described above with respect to FIGS. 1, 2, 3 and 4. For example, during the Blue/Cyan-Green eye test 600d, first optotypes may be displayed on the first display portion having green background color, and second optotypes may be displayed on the second display portion having a background color variable between blue and cyan range, as described above with respect to FIGS. 1, 2, 3 and 4. The Blue/Cyan-Green eye test 600d result may include a numeric continuous output indicative of a hyperopic correction required for the subject's eye. The Blue/Cyan-Green eye test 600d may also provide no result, for example if the outcome of the Red-Green eye test 600c for the subject is "Red" meaning that no hyperopic correction for the subject's eye is required.

Figure 6E:
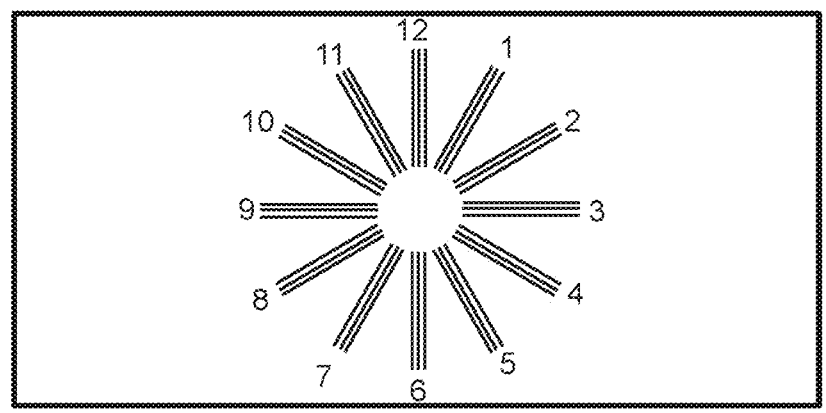

In some embodiments, the multi-step method may include a Fan eye test. One example of a Fan eye test 600e is shown in FIG. 6E. For example, a Fan eye test 600e result may include a numeric continuous output indicative of the presence of astigmatism and/or axis and/or magnitude of astigmatism of the subject's eye.

The multi-step method may include performing two or more of eye tests 600a-600e for a subject, and determining, based on the eye tests results and using the predefined prediction model, one or more components of a prescription for a subject's eyewear. In some embodiments, the prediction model may further determine a statistical probability for the one or more components of the prescription for the subject's eyewear. The multi-step method may include additional or different eye tests, as well as different number of eye tests as shown or described with respect to FIGS. 6A-6E.

The multi-step method may be performed by a system such as system 100 or system 300 described hereinabove with respect to FIGS. 1 and 3.

Reference is now made to FIGS. 7, 8, 9 and 10, showing experimental results obtained during clinical trials to evaluate the multi-step method, according to some embodiments of the invention.

The description below provides experimental results obtained during clinical trials to evaluate the multi-step method 600a-600e described above with respect to FIGS. 6A-6E and the prediction model determined based on the experimental results.

The clinical trials included preliminary small-scale trials of ~40 participants, followed by the large-scale trials of ~130 participants. In the preliminary small-scale trials, the prescription (Rx) error of the participants has been induced using lenses of over/under correction to provide an initial foundation for a prediction model. In a following large-scale clinical trial, the multi-step method (e.g., as described above with respect to FIGS. 6A-6E) has been performed on participants wearing their habitual eyewear, followed by a full eye refraction examination conducted by an optometrist. The differences in Rx between the patient's habitual eyewear and the updated Rx, provided an objective indication for the patient's Rx error. Based on the data obtained from the multi-step method, the statistical weight and strength of each of the eye tests 600a-600e has been calculated, resulting in a prediction model for a final evaluation of Rx error. Comparison of the predicted Rx error as obtained by the prediction model to the known error as provided by the full eye examination established the strength and statistically significance of the prediction model, as described hereinbelow.

Figure 7:
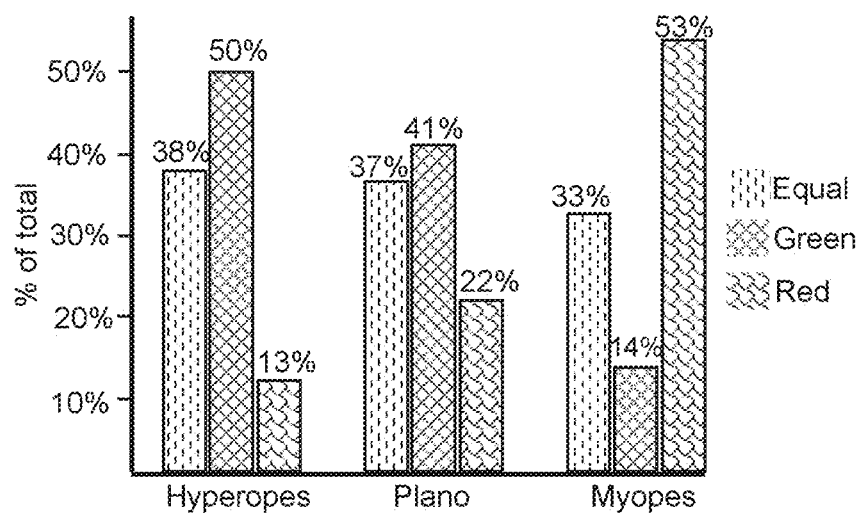

FIG. 7 shows experimental results of the Red-Green test 600c obtained in the large-scale clinical trial described hereinabove, according to some embodiments of the invention. The results of the Red-Green test 600c show a statistically significant correlation ($p<0.001$) between the Red-Green test 600c results and the participants' Rx error, with "Red" test output being dominant output for myopic participants, and "Green" being dominant output for Plano (corrected participants) and hyperope participants.

Based on the Red-Green test 600c results, three preliminary prediction models have been determined, each for one of "Red", "Green", and "Equal" test outputs. FIG. 8 shows an example of a preliminary model determined based on Red-Green test 600c results for "Green" test output obtained in the large-scale clinical trial described hereinabove, according to some embodiments of the invention. The preliminary model as shown in FIG. 8 includes results of questionnaire 600a, Blue/Cyan-Green test 600d, participants' answers to question "how long does the subject wear their own eyewear for?", and Snellen eye test 600b, ordered by their calculated weight in the preliminary prediction model (LogWorth) and their statistical strength (PValue).

Based on the three preliminary prediction models, the prediction model has been determined. FIG. 9 shows, for example, outputs of the prediction model for three (3) participants participating in the large-scale clinical trial described hereinabove, according to some embodiments of the invention. The prediction model has been determined based on the three preliminary models and based on results of the eye tests 600a-600e of the multi-step method obtained in the large-scale clinical trial described hereinabove. The outputs of the prediction model may also include the statistical probability of each of the outputs thereof (e.g., as shown in FIG. 9).

FIG. 10 shows, for example, outputs of the prediction model for four (4) participants participating in the large-scale clinical trial described hereinabove, according to some embodiments of the invention. The outputs of the prediction model may also include the statistical probability of each of the outputs thereof (e.g., as shown in FIG. 10).

The disclosed multi-step method of determining one or more components of a prescription (Rx) for a subject's eyewear utilizes a prediction model that is based on the weighted calculation of five (5) eye tests. The multi-step method may be conducted remotely (e.g., at a subject's home) or at an optometrist's clinic. The eye tests of the multi-step method may be performed with the subject wearing their current eyewear. The multi-step method may provide a tool for the optometrist to evaluate the subject's current eyewear and/or the subject's refractive error. Based on the results of eye tests of the multi-step method and using the prediction model the Rx error may be determined, optionally with percentage of confidence level for the prediction.

The Rx evaluation using the multi-step method described hereinabove may provide an objective integration of the eye tests of the multi-step method. This in contrast to standard prior art refraction procedures, during which the optometrist conducts various vision tests and evaluates the patient's Rx based on his/her subjective interpretation of the data from these tests based on his/her experience and skills.

Some embodiments of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram or portions thereof.

These computer program instructions can also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram portion or portions thereof. The computer program instructions can also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram portion or portions thereof.

The aforementioned flowchart and diagrams illustrate the architecture, functionality, and operation of possible implementations of systems, methods and computer program products according to various embodiments of the present invention. In this regard, each portion in the flowchart or portion diagrams can represent a module, segment, or portion of code, which includes one or more executable instructions for implementing the specified logical function(s). It should also be noted that, in some alternative implementations, the functions noted in the portion can occur out of the order noted in the figures. For example, two portions shown in succession can, in fact, be executed substantially concurrently, or the portions can sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment", "certain embodiments" or "some embodiments" do not necessarily all refer to the same embodiments. Although various features of the invention can be described in the context of a single embodiment, the features can also be provided separately or in any suitable combination. Conversely, although the invention can be described herein in the context of separate embodiments for clarity, the invention can also be implemented in a single embodiment. Certain embodiments of the invention can include features from different embodiments disclosed above, and certain embodiments can incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A system for automatically evaluating a vision of a subject, the system comprising:
   a processing unit configured to:
   vary with time a second wavelength value within a wavelength range of 400-540 nanometers or within a wavelength range of 560-740 nanometers so as to vary with time a second background color of a second portion of a display and continue causing a first portion of the display to emit light having a first wavelength value within a range of 480-600 nanometers so as to continue causing the first portion to present a first background color;
   obtain an input that a subject's perception of second optotypes being presented on the second portion emitting light having the second wavelength value and presenting the second background color is the same as a subject's perception of first optotypes being presented on the first portion emitting light having the first wavelength value and presenting the first background color;
   determine the second wavelength value for which the input has been obtained; and
   determine a refractive error for the subject based on the determined second wavelength value.

2. The system of claim 1, wherein the processing unit is further configured to determine one or more components of a prescription for a subject's eyewear based on the second wavelength value for which the input has been obtained.

3. The system of claim 1, wherein the processing unit is further configured to vary the second wavelength value within the predefined wavelengths range at a second wavelength value variation rate.

4. The system of claim 3, wherein the processing unit is further configured to set the second wavelength value variation rate so that a time interval during which the second wavelength is set to a particular value does not exceed 300 milliseconds.

5. The system of claim 1, wherein the processing unit is further configured to vary the second wavelength value according to an input from the subject or from a third authorized party.

6. The system of claim 1, wherein the processing unit is further configured to alternately and repeatedly present the first optotypes and the second optotypes during a first time interval and stop the presentation thereof for a second time interval.

7. The system of claim 6, wherein the processing unit is further configured to set the first time interval so that the first time interval does not exceed 300 milliseconds.

8. The system of claim 1, wherein the processing unit is further configured to receive from the subject the input that the subject's perception of the second optotypes is the same as the subject's perception of the first optotypes.

9. The system of claim 1, wherein the processing unit is interfaceable with a gaze tracking device, wherein the gaze tracking device is configured to:
   track a gaze of the subject with respect to the first optotypes being displayed on the first display portion; and
   track a gaze of the subject with respect to the second optotypes being displayed on the second display portion; and
   wherein the processing unit is further configured to:
   obtain a first gaze dataset determined based on the gaze of the subject being tracked with respect to the first optotypes;
   obtain a second gaze dataset determined based on the gaze of the subject being tracked with respect to the second optotypes; and
   determine the input that the subject's perception of the second optotypes is the same as the subject's perception of the first optotypes based on at least a portion of the first gaze dataset and at least a portion of the second gaze dataset.

10. The system of claim 1, wherein the processing unit is further configured to:
    perform an initial screening to gather a personal information concerning the subject; and
    determine the first wavelength value, an initial second wavelength value and the wavelengths range within which the second wavelength value is variable with time based on the personal information.

11. A system for automatically evaluating a vision of a subject, the system comprising:
a processing unit configured to:
cause a display to define a first display portion and a second display portion;
cause the first display portion to present a background having a first background color, the first background color within a range of 480-600 nanometers;
cause the second display portion to present a background having a second background color;
cause the display to present, on the first display portion having the first background color, one or more first optotypes;
cause the display to present, on the second display portion having the second background color, one or more second optotypes;
vary with time the second background color of the second display portion within a background colors range of 400-540 nanometers or within a background colors range of 560-740 nanometers and continue causing the first display portion to present the first background color;
obtain an input that a subject's perception of the all of the second optotypes being presented on the second display portion presenting the second background color is the same as a subject's perception of all of the first optotypes being presented on the first display portion presenting the first background color;
determine the second background color for which the input has been obtained; and
determine a refractive error for the subject based on the determined second background color.

12. The system of claim 11, wherein the processing unit is further configured to determine one or more components of a prescription for a subject's eyewear based on the second background color for which the input has been obtained.

13. The system of claim 11, wherein the processing unit is further configured to vary the second background color within the predefined background colors range at a second background color variation rate.

14. The system of claim 13, wherein the processing unit is further configured to set the second background color variation rate so that a time interval during which the second background color is set to a particular value does not exceed 300 milliseconds.

15. The system of claim 11, wherein the processing unit is further configured to vary the second background color according to an input from the subject or from a third authorized party.

16. The system of claim 11, wherein the processing unit is further configured to alternately and repeatedly present the one or more first optotypes and the one or more second optotypes during a first time interval and stop the presentation thereof for a second time interval.

17. The system of claim 16, wherein the processing unit is further configured to set the first time interval so that the first time interval does not exceed 300 milliseconds.

18. The system of claim 11, wherein the processing unit is further configured to receive from the subject the input that the subject's perception of all of the second optotypes is the same as the subject's perception of all of the first optotypes.

19. The system of claim 11, wherein the processing unit is interfaceable with a gaze tracking device, the gaze tracking device is configured to:
track a gaze of the subject with respect to the one or more first optotypes being displayed on the first display portion; and
track a gaze of the subject with respect to the one or more second optotypes being displayed on the second display portion; and
wherein the processing unit is further configured to:
obtain a first gaze dataset determined based on the gaze of the subject being tracked with respect to the one or more first optotypes;
obtain a second gaze dataset determined based on the gaze of the subject being tracked with respect to the one or more second optotypes; and
determine the input that the subject's perception of all of the second optotypes is the same as the subject's perception of all of the first optotypes based on at least a portion of the first gaze dataset and at least a portion of the second gaze dataset.

20. The system of claim 11, wherein the processing unit is further configured to:
perform an initial screening to gather a personal information concerning the subject; and
determine the first background color, an initial second background color and the background colors range within which the second background color is variable with time based on the personal information.

* * * * *